United States Patent [19]

Kondo et al.

[11] Patent Number: 4,748,148

[45] Date of Patent: May 31, 1988

[54] RECORDING SYSTEM UTILIZING PHTHALIDE DERIVATIVES AS COLORLESS CHROMOGENIC MATERIAL

[76] Inventors: Mitsuru Kondo, Kawabegun; Tomoyuki Okimoto, Amagasaki; Nobuo Kanda, all of c/o Kanzaki Paper Manufacturing Co., Ltd. 1-11 Motomachi, Jyokoji, Amagasaki, Hyogo, Japan

[21] Appl. No.: 929,786

[22] Filed: Nov. 13, 1986

Related U.S. Application Data

[60] Division of Ser. No. 667,805, Nov. 2, 1984, Pat. No. 4,641,160, which is a continuation of Ser. No. 366,338, Apr. 7, 1982, abandoned.

[30] Foreign Application Priority Data

Apr. 8, 1981 [JP] Japan .................. 56-53678

[51] Int. Cl.$^4$ .................. B41M 5/16; B41M 5/18; B41M 5/22
[52] U.S. Cl. .................. 503/220; 427/151; 503/217
[58] Field of Search .................. 346/220, 221, 225; 427/150-152; 549/224, 307; 503/217, 220, 221, 225

[56] References Cited

U.S. PATENT DOCUMENTS

| | | | |
|---|---|---|---|
| 4,020,056 | 4/1977 | Farber | 346/220 |
| 4,022,771 | 5/1977 | Farber | 346/220 |
| 4,107,428 | 8/1978 | Farber | 346/220 |
| 4,119,776 | 10/1978 | Farber | 346/220 |

FOREIGN PATENT DOCUMENTS 0062544 10/1982 European Pat. Off. ............ 346/220

*Primary Examiner*—Bruce H. Hess
*Attorney, Agent, or Firm*—Fisher, Christen & Sabol

[57] ABSTRACT

A new phthalide derivative useful as a colorless chromogenic material has the general formula:

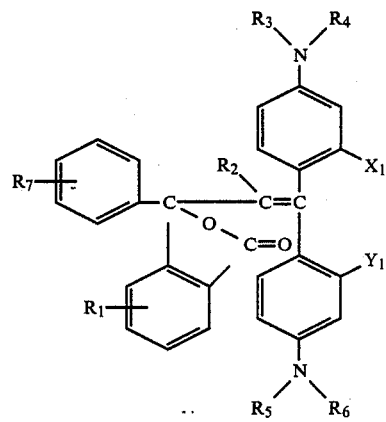

or

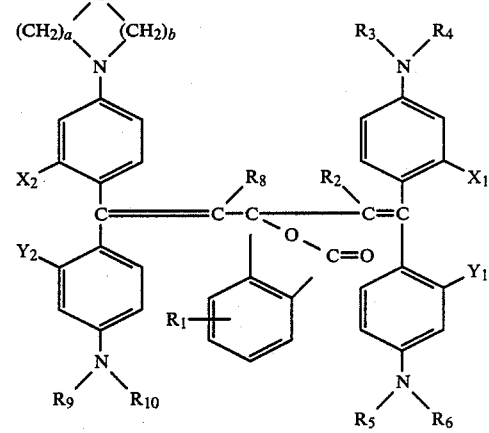

wherein $R_1$ to $R_{10}$, $X_1$, $X_2$, $Y_1$, $Y_2$, Z, a and b have the same meaning as defined hereinbefore.

7 Claims, No Drawings

RECORDING SYSTEM UTILIZING PHTHALIDE DERIVATIVES AS COLORLESS CHROMOGENIC MATERIAL

This is a divisional application of application Ser. No. 667,805, filed Nov. 2, 1984, now U.S. Pat. No. 4,641,160, which is a continuation of Ser. No. 366,338, filed Apr. 7, 1982, now abandoned.

BACKGROUND OF THE INVENTION

This invention relates to phthalide derivatives as new compounds useful as colorless chromogenic materials, a new process for preparing the same, and a new recording system utilizing the same.

There are known various kinds of recording systems utilizing the colorforming reaction between a colorless chromogenic material and an electron accepting acidic reactant material by the medium of mechanical, heat, electric or light energy. Among them there are included a pressure sensitive record sheet, a heat sensitive record sheet, an electrothermal record sheet, an ultrasonic record sheet, an electron beam record sheet, an electrostatic record sheet and a photosensitive record sheet. The colorless chromogenic materials of these kinds also find their usefulness in typewriter ribbons, ball-point pen ink, crayon and stamp ink.

One of the most typical colorless chromogenic materials is crystal violet lactone. This dye material reacts with an electron accepting acidic reactant material upon contact to develop a clear color of bluish violet but the developed color has a poor light resistance so that the recording images (color images) soon disappear in a short time when subjected to radiation of ultraviolet rays of day light. Another disadvantage of this type of dye is in the fact that the recorded images obtained with this material show no absorption for the infrared range of 700–900 nm and accordingly this type of dye material cannot be used for a reading machine utilizing an optical reading system responsive to infrared absorption.

The primary object of the invention is to provide novel phthalide derivatives useful as colorless chromogenic materials for use in various recording systems.

Another object of the invention is to provide novel colorless chromogenic materials for use in recording systems in which the color images when developed therefrom have a good light resistance, especially, a good ultraviolet ray resistance.

A further object of the invention is to provide novel colorless chromogenic materials for use in recording systems in which the color images when developed therefrom show a good absorption for infrared rays.

A still further object of the invention is to provide a novel process for preparing phthalide derivatives of the kind described above.

It is also included among the objects of the invention to provide an improved recording system in which a phthalide derivative as a new compound is used as a colorless chromogenic material and the color images when developed therefrom have a good light resistance and show a good absorption for infrared rays.

Other objects and advantages of the invention will become apparent from the following description.

SUMMARY OF THE INVENTION

The novel phthalide derivatives according to the invention has the general formula:

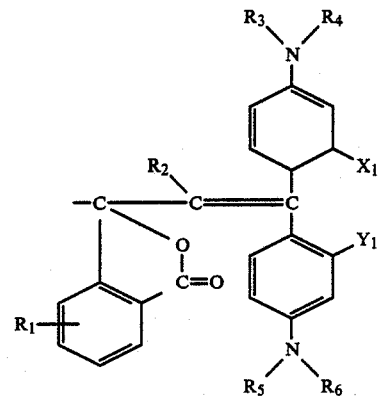

wherein $R_1$ is hydrogen or at least one substituent selected from the group consisting of halogen, alkyl, alkoxyl, nitro, amino and substituted amino; $R_2$ is hydrogen or alkyl; each $R_3$, $R_4$, $R_5$ and $R_6$ is hydrogen, alkyl, aralkyl, substituted aralkyl, aryl or substituted aryl, or, one or both of $R_3$ and $R_4$ together with the adjacent nitrogen may form a heterocyclic ring and one or both of $R_5$ and $R_6$ together with the adjacent nitrogen may form a heterocyclic ring; each $X_1$ and $Y_1$ is hydrogen, alkyl or alkoxyl; and A has any of the following general formulae (I) and (II):

wherein $R_7$ is hydrogen or one of four substituents selected from the group consisting of halogen, alkyl, alkoxyl, nitro and alicyclic amino having the further general formula:

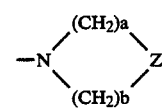

wherein Z is oxygen or methylene; and each a and b is an integer of 1 to 3 (but $a+b \geq 3$), and

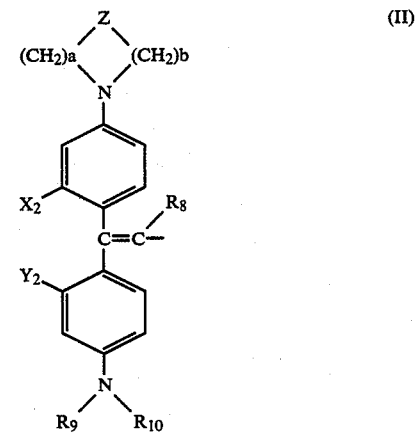

wherein $R_8$ is hydrogen or alkyl; each $R_9$ and $R_{10}$ is hydrogen, alkyl, aralkyl, substituted aralkyl, aryl, substituted aryl, or, one or both of $R_9$ and $R_{10}$ together with the adjacent nitrogen may form a heterocyclic ring; each $X_2$ and $Y_2$ is hydrogen, alkyl or alkoxyl; and Z, a and b are the same as hereinabove defined.

The phthalide derivatives having the above general formula can be used as colorless chromogenic materials for use in various recording systems including a pressure sensitive recording system and a heat sensitive recording system. The compounds according to the invention can produce a color of blue to green upon contact with an electron accepting acidic reactant material. The color images produced has a good light resistance and can maintain its clear color tone initially produced for a long time. The color images produced also show a good absorption for infrared rays with the range of 700–900 nm so that they can be detected for reading in an infrared ray responsive optical reading machine.

DETAILED DESCRIPTION OF THE INVENTION

In one aspect of the invention the novel phthalide derivatives are represented by the general formula:

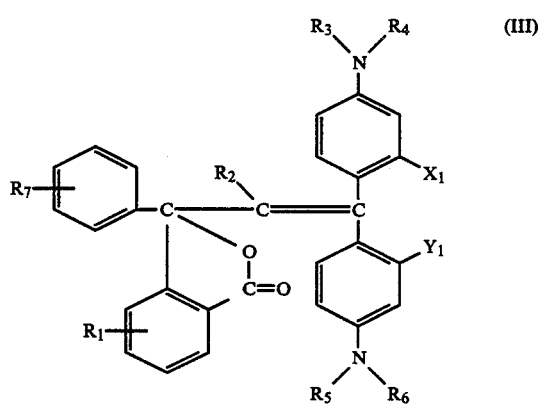

In the other aspect of the invention the novel phthalide derivatives are represented by the general formula:

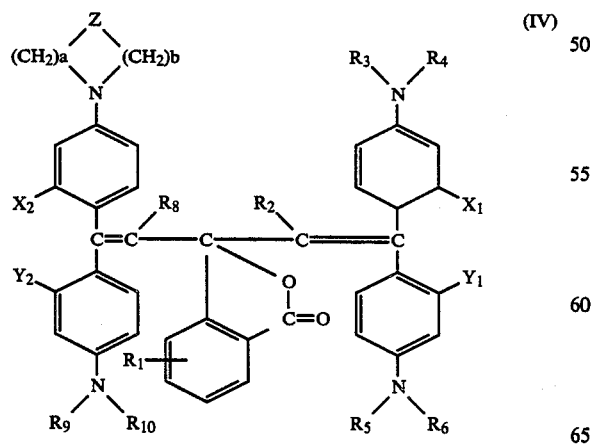

A further typical form of the above formula (IV) is as follows:

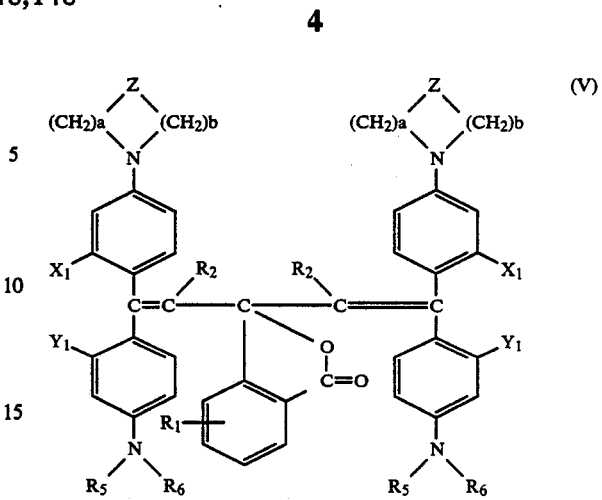

The compounds represented by the formula (III) may preferably be prepared by making benzophenone derivatives represented by the general formula (VI) react with ethylene derivatives represented by the general formula (VII) with use of dehydration condensation agents at a temperature within the range of 30° to 150° C. and for about 30 minutes to several hours:

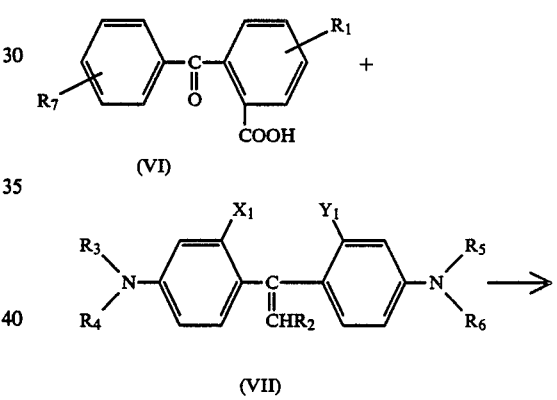

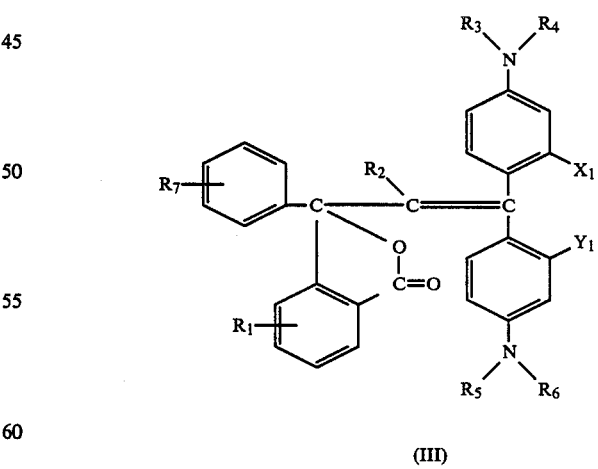

wherein $R_1$, $R_2$, $R_3$, $R_4$, $R_5$, $R_6$, $R_7$, $X_1$ and $Y_1$ are the same as described above.

In the substituted groups $R_1$ to $R_{10}$ of the phthalide derivatives according to the invention, preferably, alkyl may have 1 to 4 carbon atoms, alkoxyl may have 1 to 4 carbon atoms, aralkyl may be benzyl or phenethyl, aryl may be phenyl, and the substituted groups of each of substituted aralkyl and substituted aryl may be alkyl having 1 to 4 carbon atoms, alkoxyl having 1 to 2 carbon atoms, halogen or nitro.

The benzophenone derivatives represented by the general formula (VI) may preferably be prepared by dissolving 3-phenylphthalide derivatives represented by the general formula (VIII) and then oxidizing them with use of nitrobenzene derivatives, or, by causing condensation between benzene derivatives represented by the general formula (IX) and phthalic anhydride derivatives represented by the general formula (X) in the presence of Friedel-Crafts Type Catalysts:

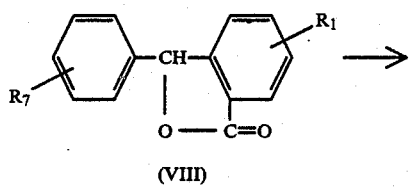

(VIII)

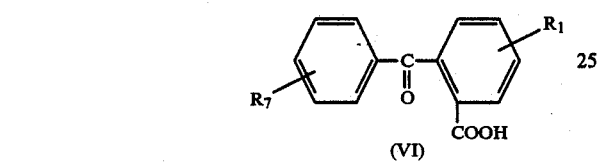

(VI)

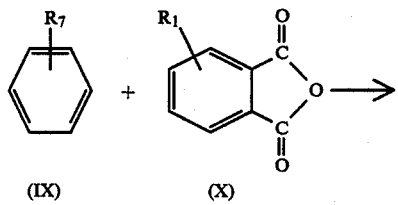

(IX)    (X)

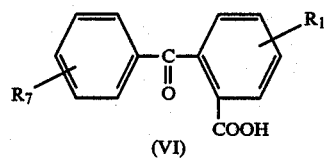

(VI)

wherein $R_1$ and $R_7$ are the same as described above.

The conpounds represented by the general formula (IV) may preferably be prepared by causing reaction between benzoic acid derivatives represented by the general formula (XI) and ethylene derivatives represented by the general formula (VII) with use of dehydration condensation agents at a temperature within the range of 30° to 150° C. and for about 30 minutes to several hours:

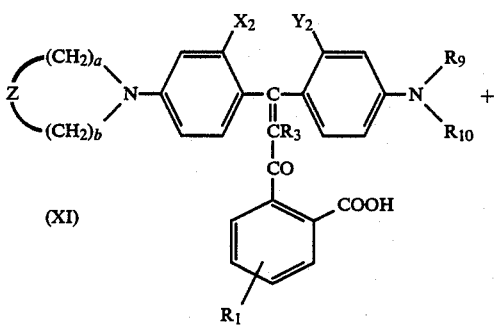

(XI)

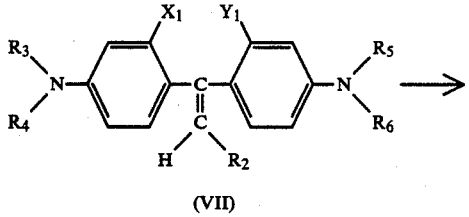

(VII)

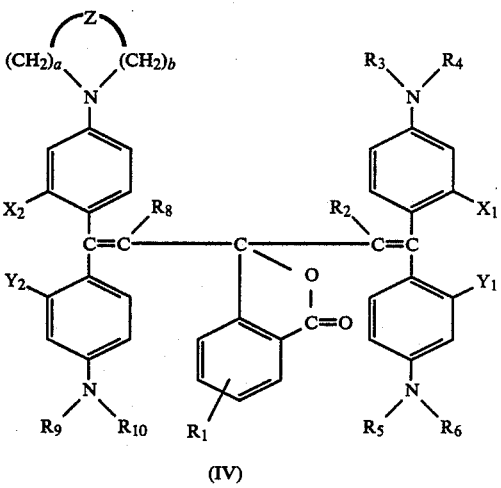

(IV)

wherein $R_1$, $R_2$, $R_3$, $R_4$, $R_5$, $R_6$, $R_8$, $R_9$, $R_{10}$, $X_1$, $X_2$, $Y_1$, $Y_2$, Z, a and b are the same as described above.

The above benzoic acid derivatives may preferably be prepared by causing condensation between phthalic anhydride derivatives represented by the general formula (X) and ethylene derivatives represented by the general formula (XII) with use of Friedel-Crafts Type Catalysts:

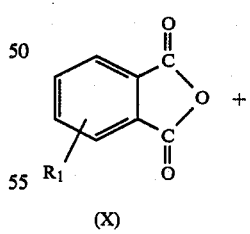

(X)

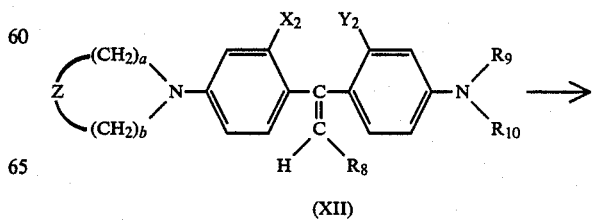

(XII)

-continued

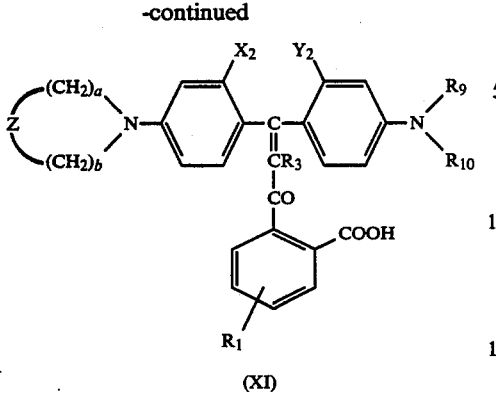

(XI)

wherein $R_1$, $R_8$, $R_9$, $R_{10}$, $X_2$, $Y_2$, Z, a and b are the same as described above.

The compounds represented by the general formula (IV) may also be prepared by causing condensation between phthalic anhydride derivatives represented by the general formula (X) and ethylene derivatives represented by the general formula (VII) and making the condensation products with ethylene derivatives represented by the general formula (XII).

The compounds represented by the general formula (V) may also preferably be prepared by making phthalic anhydride derivatives represented by the general formula (X) react with ethylene derivatives represented by the general formula (XIII) with use of dehydration condensation agents at a temperature within the range of 50° to 200° C. and for about 30 minutes to several hours:

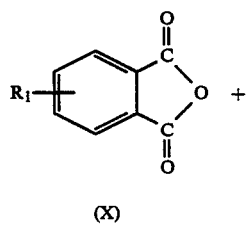

(X)

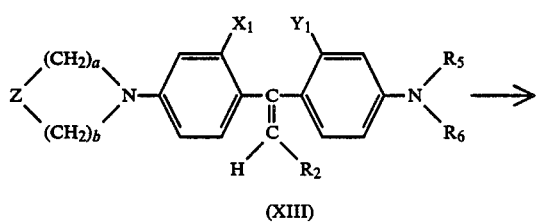

(XIII)

-continued

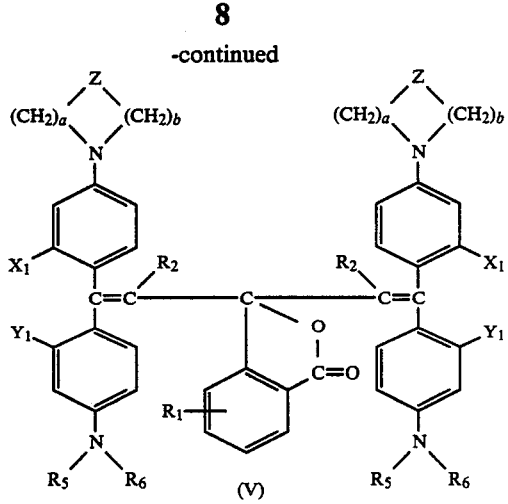

(V)

wherein $R_1$, $R_2$, $R_5$, $R_6$, $X_1$, $Y_1$, Z, a and b are the same as described above.

As the typical compounds of benzophenone derivatives represented by the above mentioned general formula (VI) which are used in this invention, the following compounds may be examplified: 2-benzoylbenzoic acid, 2-p-methylbenzoylbenzoic acid, 2-p-methoxybenzoylbenzoic acid, 2-p-pyrrolidinobenzoylbenzoic acid, 2-p-piperidinobenzoylbenzoic acid, 2-p-hexamethyleneiminobenzoylbenzoic acid, 2-p-morpholinobenzoylbenzoic acid, 2-benzoyl-5-dimethylaminobenzoic acid, 2-o(or m or p)-methylbenzoyl-5-dimethylaminobenzoic acid, 2-o(or m or p)-methoxybenzoyl-5-dimethylaminobenzoic acid, 2-o(or m or p)-chlorobenzoyl-5-dimethylaminobenzoic acid, 2-o(or m or p)-nitrobenzoyl-5-dimethylaminobenzoic acid, 2-p-pyrrolidinobenzoyl-5-dimethylaminobenzoic acid, 2-p-piperidinobenzoyl-5-dimethylaminobenzoic acid, 2-p-hexamethyleneiminobenzoil-5-dimethylaminobenzoic acid, 2-[2,4(or 3,4)-dimethyl]benzoyl-5-dimethylaminobenzoic acid, 2-[2,4(or 3,4)-dimethoxy]benzoyl-5-dimethylaminobenzoic acid, 2-[2,4(or 3,4)-dichloro]benzoyl-5-dimethylaminobenzoic acid, 2-(2-methyl-4-methoxy)benzoyl-5-dimethylaminobenzoic acid, 2-(2-methoxy-4-methyl)benzoyl-5-dimethylaminobenzoic acid, 2-p-methoxybenzoyl-5-diethylaminobenzoic acid, 2-p-methoxybenzoyl-5-(N-ethyl-N-benzyl)aminobenzoic acid, 2-p-methoxybenzoyl-5-(N-methyl-N-p-chlorobenzyl)aminobenzoic acid, 2-p-methoxybenzoyl-5-(N-methyl-N-phenyl)aminobenzoic acid, 2-p-methoxybenzoyl-5-(N-methyl-N-p-tolyl)aminobenzoic acid, 2-p-methoxybenzoyl-5-diallylaminobenzoic acid, 2-p-methoxybenzoyl-5-pyrrolidinobenzoic acid, 2-p-methoxybenzoyl-5-piperidinobenzoic acid, 2-p-pyrrolidinobenzoyl-5-ethoxybenzoic acid, 2-p-pyrrolidinobenzoyl-5-pyrrolidinobenzoic acid, 2-p-pyrrolidinobenzoyl-4-chloro-5-dimethylaminobenzoic acid, 2-p-pyrrolidinobenzoyl-4-chlorobenzoic acid, 2-p-pyrrolidinobenzoyl-5-chlorobenzoic acid, 2-p-pyrrolidinobenzoyl-4,5-dichlorobenzoic acid, 2-p-pyrrolidinobenzoyl-3,4,5,6-tetrachlorobenzoic acid, 2-p-pyrrolidinobenzoyl-4-nitrobenzoic acid, 2-p-pyrrolidinobenzoyl-5-nitrobenzoic acid and the like.

Among the typical compounds of ethylene derivatives represented by the above described general formula (VII) which are used in this invention there may be included the following compounds: 1,1-bis(p-aminophenyl)ethylene, 1,1-bis(p-methylaminophenyl)ethylene, 1,1-bis(p-dimethylaminophenyl)ethylene, 1,1-bis(p-ethylaminophenyl)ethylene, 1,1-bis(p-diethylaminophenyl)-ethylene, 1,1-bis(p-dimethylaminophenyl)-1-propene, 1,1-bis(p-diethylaminophenyl)-1-propene, 1,1-bis(4-dimethylamino-2-methylphenyl)ethylene, 1,1-bis(4-diethylamino-2-methylphenyl)ethylene, 1,1-bis(4-dimethylamino-2-methoxyphenyl)ethylene, 1,1-bis(4-diethylamino-2-methoxyphenyl)ethylene, 1,1-bis[p-(N-methyl-N-benzyl)aminophenyl]ethylene, 1,1-bis[p-(N-ethyl-N-benzyl)aminophenyl]ethylene, 1,1-bis[p-(N-ethyl-N-p-chlorobenzyl)aminophenyl]ethylene, 1,1-bis[p-(N-methyl-N-phenyl)aminophenyl]ethylene, 1,1-bis[p-(N-methyl-N-p-tolyl)aminophenyl]ethylene, 1,1-bis[p-(N-methyl-N-p-methoxyphenyl)aminophenyl]ethylene, 1,1-bis[p-(N-ethyl-N-p-methoxyphenyl)aminophenyl]ethylene, 1,1-bis(4-dimethylamino-2-methylphenyl)-1-propene, 1,1-bis-(4-diethylamino-2-methylphenyl)-1-propene, 1,1-bis(4-dimethylamino-2-methoxyphenyl)-1-propene, 1,1-bis(4-diethylamino-2-methoxyphenyl)-1-propene, 1-(4-dimethylaminophenyl)-1-(4-diethylaminophenyl)ethylene, 1-(4-dimethylaminophenyl)-1-(4-diethylamino-2-methylphenyl)ethylene, 1-(4-dimethylaminophenyl)-1-(4-diethylamino-2-methoxyphenyl)ethylene, 1-(4-dimethylaminophenyl)-1-(4-N-benzyl-N-ethylaminophenyl)ethylene, 1-(4-dimethylaminophenyl)-1-[4-(N-p-tolyl-N-methyl)aminophenyl]ethylene, 1,1-bis(4-pyrrolidinophenyl)ethylene, 1,1-bis(4-piperidinophenyl)ethylene, 1,1-bis(4-morpholinophenyl)ethylene, 1,1-bis(4-hexamethyleneiminophenyl)ethylene, 1,1-bis(2-methyl-4-pyrrolidinophenyl)ethylene, 1,1-bis(2-methyl-4-piperidinophenyl)ethylene, 1,1-bis(2-methyl-4-morpholinophenyl)ethylene, 1,1-bis(2-methyl-4-hexamethyleneiminophenyl)ethylene, 1,1-bis(2-methoxy-4-pyrrolidinophenyl)ethylene, 1,1-bis(2-methoxy-4-piperidinophenyl)ethylene, 1,1-bis(2-methoxy-4-morpholinophenyl)ethylene, 1,1-bis(2-methoxy-4-hexamethyleneiminophenyl)ethylene, 1-(4-pyrrolidinophenyl)-1-(4-dimethylaminophenyl)ethylene, 1-(4-piperidinophenyl)-1-(4-dimethylaminophenyl)ethylene, 1-(4-morpholinophenyl)-1-(4-dimethylaminophenyl)ethylene, 1-(4-hexamethyleneiminophenyl)-1-(4-dimethylaminophenyl)ethylene, 1-(4-pyrrolidinophenyl)-1-(4-N-ethyl-N-benzylaminophenyl)ethylene, 1-(4-piperidinophenyl)-1-(4-N-ethyl-N-benzylaminophenyl)ethylene, 1-(4-morpholinophenyl)-1-(4-N-ethyl-N-benzylaminophenyl)ethylene, 1-(4-hexamethyleneiminophenyl)-1-(4-N-ethyl-N-benzylaminophenyl)ethylene, 1-(4-pyrrolidinophenyl)-1-(4-N-methyl-N-p-tolylaminophenyl)ethylene, 1-(4-piperidinophenyl)-1-(4-N-methyl-N-p-tolylaminophenyl)ethylene, 1-(4-morpholinophenyl)-1-(4-N-methyl-N-p-tolylaminophenyl)ethylene, 1-(4-hexamethyleneiminophenyl)-1-(4-N-methyl-N-p-tolylaminophenyl)ethylene, 1-(4-pyrrolidinophenyl)-1-(2-methyl-4-diethylaminophenyl)ethylene, 1-(4-pyrrolidinophenyl)-1-(2-methoxy-4-diethylaminophenyl)ethylene, 1,1-bis(4-pyrrolidinophenyl)-1-propene, 1,1-bis(4-piperidinophenyl)-1-propene, 1,1-bis(4-morpholinophenyl)-1-propene, 1,1-bis(4-hexamethyleneiminophenyl)-1-propene and the like.

Among the typical compounds of phthalic anhydride derivatives represented by the above mentioned general formula (X) which are used in this invention there may be included the following compounds: phthalic anhydride, 3(or 4)-chlorophthalic anhydride, 4,5-dichlorophthalic anhydride, 3,4,5,6-tetrachlorophthalic anhydride, 3(or 4)-bromophthalic anhydride, 4,5-dibromophthalic anhydride, 3,4,5,6-tetrabromophthalic anhydride, 4-methylphthalic anhydride, 4-methoxyphthalic anhydride, 4-ethoxyphthalic anhydride, 3(or 4)-nitrophthalic anhydride, 3(or 4)-dimethylaminophthalic anhydride, 3(or 4)-diethylaminophthalic anhydride, 4-(N-ethyl-N-benzyl)aminophthalic anhydride, 4-(N-methyl-N-phenyl)aminophthalic anhydride, 4-pyrrolidinophthalic anhydride, 4-piperidinophthalic anhydride and the like.

Among the typical compounds of ethylene derivatives represented by the above described general formula (XII) and (XIII) which are used in this invention there may be included the following compounds: 1,1-bis(4-pyrrolidinophenyl)ethylene, 1,1-bis(4-piperidinophenyl)ethylene, 1,1-bis(4-morpholinophenyl)ethylene, 1,1-bis(4-hexamethyleneiminophenyl)ethylene, 1,1-bis(2-methyl-4-pyrrolidinophenyl)ethylene, 1,1-bis(2-methyl-4-piperidinophenyl)ethylene, 1,1-bis(2-methyl-4-morpholinophenyl)ethylene, 1,1-bis(2-methyl-4-hexamethyleneiminophenyl)ethylene, 1,1-bis(2-methoxy-4-pyrrolidinophenyl)ethylene, 1,1-bis(2-methoxy-4-piperidinophenyl)ethylene, 1,1-bis(2-methoxy-4-morpholinophenyl)ethylene, 1,1-bis(2-methoxy-4-hexamethyleneiminophenyl)ethylene, 1-(4-pyrrolidinophenyl)-1-(4-dimethylaminophenyl)ethylene, 1-(4-piperidinophenyl)-1-(4-dimethylaminophenyl)ethylene, 1-(4-morpholinophenyl)-1-(4-dimethylaminophenyl)ethylene, 1-(4-hexamethyleneiminophenyl)-1-(4-dimethylaminophenyl)ethylene, 1-(4-pyrrolidinophenyl)-1-(4-N-ethyl-N-benzylaminophenyl)ethylene, 1-(4-piperidinophenyl)-1-(4-N-ethyl-N-benzylaminophenyl)ethylene, 1-(4-morpholinophenyl)-1-(4-N-ethyl-N-benzylaminophenyl)ethylene, 1-(4-hexamethyleneiminophenyl)-1-(4-N-ethyl-N-benzylaminophenyl)ethylene, 1-(4-pyrrolidinophenyl)-1-(4-N-methyl-N-p-tolylaminophenyl)ethylene, 1-(4-piperidinophenyl)-1-(4-N-methyl-N-p-tolylaminophenyl)ethylene, 1-(4-morpholinophenyl)-1-(4-N-methyl-N-p-tolylaminophenyl)ethylene, 1-(4-hexamethyleneiminophenyl)-1-(4-N-methyl-N-p-tolylaminophenyl)ethylene, 1-(4-pyrrolidinophenyl)-1-(2-methyl-4-diethylaminophenyl)ethylene, 1-(4-pyrrolidinophenyl)-1-(2-methoxy-4-diethylaminophenyl)ethylene, 1,1-bis(4-pyrrolidinophenyl)-1-propene, 1,1-bis(4-piperidinophenyl)-1-propene, 1,1-bis(4-morpholinophenyl)-1-propene, 1,1-bis(4-hexamethyleneiminophenyl)-1-propene and the like.

The dehydration condensation agents which are used for carrying out the reaction between benzophenone derivatives represented by the general formula (VI) and ethylene derivatives represented by the general formula (VII), the reaction between phthalic anhydride derivatives represented by the general formula (X) and ethylene derivatives represented by the general formula (VIII), and, the reaction between benzoic acid derivatives represented by the general formula (XI) and ethylene derivatives represented by the general formula (VII) may preferably have a function as a solvent. Among the typically useful dehydration condensation agents for this purpose there are included lower fatty acid anhydride, e.g., acetic anhydride and propionic anhydride, and inorganic acid, e.g., phosphorus oxychloride, phosphorus trichloride, sulfuric acid and polyphosphoric acid. Various Friedel-Crafts Type Catalysts may also be used as dehydration condensation agents. These dehydration condensation agents may be used either solely or in combination.

The phthalide derivatives thus obtained according to the invention are substantially colorless chromogenic compounds which can develop a color upon contact with electron accepting acidic materials (hereinafter referred to as "acceptors"). They are especially advantageous in that they have a good light resistance and show a good absorption for infrared rays. Accordingly, they find their usefulness in use for the production of various kinds of record materials.

The above mentioned phthalide derivatives may be used either solely or in combination or, when desired, together with any of the following basic dye compounds: triarylmethanelactone compounds such as 3,3-bis(p-dimethylaminophenyl)-6-dimethylaminophthalide, 3-(p-dibenzylaminophenyl)-3-(1,2-dimethylindole-3-yl)-7-azaphthalide, 3-(4-diethylamino-2-ethoxyphenyl)-3-(1-ethyl-2-methylindole-3-yl)-7-azaphthalide and 3,3-bis(1-ethyl-2-methylindole-3-yl)phthalide; fluoran compounds such as 3-diethylamino-6-methylfluoran, 3-diethylamino-6-methyl-7-chlorofluoran, 3-(N-ethyl-N-p-tolylamino)-7-methylfluoran, 3-diethylamino-6-methyl-7-anilinofluoran, 3-(N-cyclohexyl-N-methylamino)-6-methyl-7-anilinofluoran, 3-(N-ethyl-N-p-tolylamino)-6-methyl-7-anilinofluoran, and 3-diethylamino-7-o-chloroanilinofluoran; spiropyran compounds such as di-$\beta$-naphthospiropyran and 3-methyl-di-$\beta$-naphthospiropyran; diphenylmethane compounds such as 4,4'-bis-dimethylaminobenzhydrylbenzyl ether, and 4,4'-bis-dimethylaminophenyl-p-toluenesulfinic acid ester; azine compounds such as 3,7-bis(dimethylamino)-10-benzoylphenothiazine and 3,7-bis(diethylamino)-10-benzoylphenoxazine; triarylmethane compounds such as N-butyl-3-[bis{4-(N-methylanilino)-phenyl}methyl]carbazole.

The acceptors used are selected according to the kinds of record materials. The materials which are preferably used as acceptors for pressure sensitive record materials, heat sensitive record materials, electrothermal record material, ultrasonic record materials, electrostatic record materials, typewriter ribbons, ball-point pen ink and crayon are those which function as Brønsted or Lewis acid. Among them there are included: inorganic acceptors such as acid clay, activated clay, attapulgite, bentonite, colloidal silica, aluminum silicate, magnesium silicate, zinc silicate, tin silicate, calcined kaolin and talc; organic acceptors such as aliphatic carboxylic acids, e.g., oxalic acid, maleic acid, tartaric acid, citric acid, succinic acid and stearic acid, aromatic carboxylic acids, e.g., benzoic acid, p-tert-butylbenzoic acid, phthalic acid, gallic acid, salicylic acid, 3-isopropylsalicylic acid, 3-phenylsalicylic acid, 3-cyclohexylsalicylic acid, 3,5-di-tert-butylsalicylic acid, 3-methyl-5-benzylsalicylic acid, 3-phenyl-5-($\alpha,\alpha$-dimethylbenzyl)salicylic acid, 3,5-di-($\alpha$-methylbenzyl)-salicylic acid and 2-hydroxy-1-benzyl-3-naphthoic acid, phenolic compounds, e.g., 4,4'-isopropylidenediphenol, 4,4'-isopropylidenebis(2-chlorophenol), 4,4'-isopropylidenebis(2,6-dibromophenol), 4,4'-isopropylidenebis(2,6-dichlorophenol), 4,4'-isopropylidenebis(2-methylphenol), 4,4'-isopropylidenebis(2,6-dimethylphenol), 4,4'-isopropylidenebis(2-tert-butylphenol), 4,4'-sec-butylidenebisphenol, 4,4'-cyclohexylidenebisphenol, 4,4'-cyclohexylidenebis(2-methylphenol), 4-tert-butylphenol, 4-phenylphenol, 4-hydroxydiphenoxide, $\alpha$-naphthol, $\beta$-naphthol, methyl-4-hydroxybenzoate, benzyl-4-hydroxybenzoate, 2,2'-thiobis(4,6-dichlorophenol), 4-tert-octylcatechol, 2,2'-methylenebis(4-chlorophenol), 2,2'-methylenebis(4-methyl-6-tert-butylphenol) and 2,2'-dihydroxydiphenyl, phenol resins, e.g., p-phenyl-phenolformaldehyde resin and p-butylphenol-acetylene resin; salts of the above organic acceptors with polyvalent metals such as zinc, magnesium, aluminium, calcium, titanium, manganese, tin and nickel; and inorganic acid such as hydrogen halide, e.g., hydrogen chloride, hydrogen bromide and hydrogen iodide, boric acid, silicic acid, phosphoric acid, sulfuric acid, nitric acid, perchloric acid and halides of aluminium, zinc, nickel, tin, titanium, boron and the like.

In case of electron beam record materials or photosensitive record materials, compounds which can produce by electron beam or light radiation hydrogen halogenides, such as hydrogen chloride, hydrogen bromide and hydrogen iodide, carboxylic acids, sulfonic acids or phenols are preferably used as acceptor materials. Among those compounds, there are included organic halogen compounds, such as carbon tetrabromide, $\alpha,\alpha,\alpha$-tribromoacetophenone, hexachloroethane, iodoform, 2-tribromomethylpyridine, trichloromethyl sulfonylbenzene, o-quinonediazido compounds, phenol esters of carboxylic acid or sulfonic acid which can cause Fries rearrangement.

Some embodiments of the utilization of the phthalide derivatives according to the invention for various kinds of record materials are described hereinbelow:

The phthalide derivatives can be utilized for various kinds of pressure sensitive record materials, e.g., those disclosed in U.S. Pat. specification Nos. 2,505,470, 2,505,471, 2,505,489, 2,548,366, 2,712,507, 2,730,456, 2,730,457, 3,418,250, 3,924,027 and 4,010,038.

A typical method for the production of a pressure sensitive record material utilizing the phthalide derivatives according to the invention is as follows:

At least one of the phthalide derivatives according to the invention is dissolved in a solvent to form a solution which may include synthetic oil such as alkylated naphthalene, alkylated diphenyl, alkylated diphenylmethane and alkylated terphenyl, vegetable oil such as cotton seed oil and castor oil, animal oil and mineral oil or mixtures of the foregoing. The solution may additionally include basic colorless chromogenic material such as triarylmethane lactones, spiropyrans, fluorans, diphenylmethanes and Leucomethylene Blue. The solution of the phthalide derivative may be dispersed in a binde to form a coating composition. The solution may be enclosed in microcapsules through the utilization of the coacervation technique, the interfacial polymerization technique, the in-situ polymerization technique or any other method for making oil droplet-containing microcapsules and the microcapsules thus prepared are dispersed in a binder to form a coating composition. Any one of the coating compositions thus prepared is applied to a base sheet such as a paper sheet, plastic sheet, resin coated paper sheet, etc. to obtain a pressure sensitive record material. In case where the pressure sensitive copying system consists of a top sheet, a bottom sheet and, if necessary, at least one middle sheet, the pressure sensitive record material according to the invention is used as the top sheet and the middle sheet. The pressure sensitive record material according to the invention also be utilized in the "self contained" system in which both the colorless chromogenic material and the acceptor are dispersed on one surface of the same sheet. The pressure sensitive record material utilizing the phthalide derivative according to the invention can produce clear color images having a good light resistance and showing a good absorption for infrared rays which enables a certain reading by an optical reading machine.

The phthalide derivatives according to the invention are also useful for production of various kinds of heat sensitive record materials, e.g., as disclosed in Japanese Patent Publication Nos. 3,680 of 1969, 27,880 of 1969, 14,039 of 1970, 43,830 of 1973, 69 of 1974, 70 of 1974 and 20,142 of 1977. Most typically, heat sensitive record materials may be produced by coating a coating composition including a binder, fine particles of the phthalide derivative according to the invention and the acceptor on a base sheet such as paper sheet, plastic film, synthetic paper sheet, woven fabric sheet or mold. The coating composition may include a suitable binder material in the range of 1 to 50 parts by weight, preferably within the range of 4 to 10 parts by weight, per one part by weight of the phthalide derivative used. The coating composition may include inorganic metal compounds such as oxides, hydroxides and carbonates of polyvalent metals and/or inorganic pigments in an amount of 0.1 to 5 parts by weight, preferably, 0.2 to 2 parts by weight, per one part by weight of the amount of the acceptor. The recording layer may also include dispersing agents, ultraviolet ray absorbing agents, heat fusible materials, antifoaming agent, fluorescent dye, coloring dyes and other adding materials. The phthalide derivative and the acceptor may be applied to a base sheet either in the form of a single coating composition or in the form of two separate coating composition which may be applied one by one. Application of the phthalide derivative and acceptor to a base sheet may also be carried out by impregnation or by sizing. The amount of the coating composition including the phthalide derivative and the acceptor may preferably be within the range of 2 to 12 g/cm². Among the useful binder materials there may be included starches, cellulose, proteins, gum arabic, polyvinyl alcohol, salts of styrene-maleic anhydride copolymer, styrene-butadiene copolymer emulsions, salts of vinyl acetate-maleic anhydride copolymer and salts of polyacrylic acid.

The electrothermal record materials may be produced according to any known methods such as those disclosed in Japanese Laid-Open Patent Publication Nos. 11,344 of 1974 and 48,930 of 1975. Usually, the record material of this type may be produced, either by coating on a base sheet such as a paper sheet a coating composition consisting of a dispersion of an electroconductive material, a basic dye material essentially comprising the phthalide derivative according to the invention, an acceptor and a binder, or by coating an electroconductive material on a basic sheet to form an electroconductive layer thereon and further coating on the electroconductive layer another coating composition consisting of a dispersion of the phthalide derivative according to the invention, an acceptor and a binder. In case where each of the phthalide derivative and the acceptor used is not fusible within the temperature range of 70° to 120° C., an appropriate heat fusible material may be added for controlling the heat sensitivity.

The photosensitive record materials in which the phthalide derivatives according to the invention are utilized may be produced in a similar manner to any of those disclosed in Japanese Patent Publication Nos. 24,188 of 1963, 10,550 of 1970, 13,258 of 1970, 204 of 1974, 6,212 of 1974 and 28,449 of 1974 and Japanese Laid-Open Patent Publication Nos. 31,615 of 1972, 32,532 of 1973, 9,227 of 1974, 135,617 of 1974, 80,120 of 1975, 87,317 of 1975 and 126,228 of 1975.

The invention is also applicable to other recording systems, such as, the ultrasonic record material, e.g., as disclosed in French Pat. specification No. 2,120,922, the electron beam recording system, e.g., as disclosed in Belgian Pat. No. 7,959,986, the electrostatic record material, e.g., as disclosed in Japanese Patent Publication No. 3,932 of 1974, the photosensitive printing material, e.g., as disclosed in Japanese Laid-Open Patent Publication No. 12,104 of 1973, the seal stamping material, e.g., as disclosed in Japanese Patent Publication No. 10,766 of 1972, type ribbons as disclosed in Japanese Laid-Open Patent Publication No. 3,713 of 1974, ball-point pen ink as disclosed in Japanese Laid-Open Patent Publication No. 83,924 of 1973 and crayon as disclosed in U.S. Pat. No. 3,769,045, by merely using the phthalide derivatives instead of the conventional basic colorless chromogenic materials.

PREFERRED EMBODIMENTS OF THE INVENTION

The following examples serve to illustrate the invention in more detail although the invention is not limited to the examples. Unless otherwise indicated, parts and % signify parts by weight and % by weight, respectively.

EXAMPLE 1

30 g of 2-p-methoxybenzoyl-5-dimethylaminobenzoic acid and 27 g of 1,1-bis(p-dimethylaminophenyl)ethylene were added to 60 g of acetic anhydride and the mixture was heated at 50°–55° C. for 30 minutes with stirring. After the termination of reaction, sodium hydroxide was added to the mixture to decompose acetic anhydride. The resultant precipitate was separated by filtration and then dissolved in hydrochloric acid. The solution was filtered and neutralized with an aqueous solution of sodium hydroxide to obtain a solid. The solid was separated by filtration, dried and recrystallized from methanol to obtain 50.3 g of 3-(p-methoxyphenyl)-3-{1,1-bis(p-dimethylaminophenyl)ethylene-2-yl}-6-dimethylaminophthalide in the form of light blue crystals having a melting point of 103°–105° C. The phthalide derivative became black blue upon contact with silica gel.

EXAMPLE 2

Example 1 was repeated except that 33 g of 2-(3,4-dimethoxy)benzoyl-5-dimethylaminobenzoic acid was used instead of 30 g of 2-p-methoxybenzoyl-5-dimethylaminobenzoic acid to obtain 52.0 g of 3-(3,4-dimethoxyphenyl)-3-{1,1-bis(p-dimethylaminophenyl)ethylene-2-yl}-6-dimethylaminophthalide in the form of light blue crystals having a melting point of 104°–107° C. The phthalide derivative became black blue upon contact with silica gel.

EXAMPLE 3

Example 1 was repeated except that 28 g of 2-p-methylbenzoyl-5-dimethylaminobenzoic acid was used instead of 30 g of 2-p-methoxybenzoyl-5-dimethylaminobenzoic acid to obtain 46.7 g of 3-(p-methylphenyl)-3-{1,1-bis(p-dimethylaminophenyl)ethylene-2-yl}-6-dimethylaminophthalide in the form of light blue crystals having a melting point of 113°–116° C. The phthalide derivative became green blue upon contact with silica gel.

EXAMPLE 4

Example 1 was repeated except that 31 g of 1-(4-dimethylaminophenyl)-1-(4-diethylamino-2-methylphenyl)ethylene was used instead of 27 g of 1,1-bis(p-dimethylaminophenyl)ethylene to obtain 32.8 g of 3-(p-methoxyphenyl)-3-{1-(4-dimethylaminophenyl)-1-(4-diethylamino-2-methylphenyl)ethylene-2-yl}-6-dimethylaminophthalide in the form of light blue crystals having a melting point of 108°–111° C. The phthalide derivative became blue green upon contact with silica gel.

EXAMPLES 5 TO 26

Example 1 was repeated except that benzophenon derivatives shown in Table 1 were used instead of 2-p-methoxybenzoyl-5-dimethylaminobenzoic acid and ethylene derivatives shown in Table 1 were used instead of 1,1-bis(p-dimethylaminophenyl)ethylene to obtain phthalide derivatives shown in Table 1. The colors formed upon contact with silica gel are shown in Table 1.

TABLE 1

| Example | Benzophenone derivatives | Ethylene derivatives | Phthalide derivatives | Color |
|---|---|---|---|---|
| 5 | (structure with NO₂, COOH, N(CH₃)₂) | (structure with two N(CH₃)₂ groups) | (phthalide structure with NO₂ and N(CH₃)₂ groups) | blue |
| 6 | (structure with Cl, COOH, N(CH₃)₂) | (structure with two N(CH₃)₂ groups) | (phthalide structure with Cl and N(CH₃)₂ groups) | blue |

TABLE 1-continued

| Example | Benzophenone derivatives | Ethylene derivatives | Phthalide derivatives | Color |
|---|---|---|---|---|
| 7 | | | | blue |
| 8 | | | | black blue |

TABLE 1-continued

| Example | Benzophenone derivatives | Ethylene derivatives | Phthalide derivatives | Color |
|---|---|---|---|---|
| 9 | 2-phenoxybenzoic acid (COOH, O, phenyl) | bis(4-dimethylaminophenyl)methylene (CH₂=C) | 3,3-bis(4-dimethylaminophenyl)-6-methylphthalide | blue |
| 10 | 4-methoxy-4'-diethylamino-2-carboxybenzophenone | bis(4-dimethylaminophenyl)methylene | 3-(4-methoxyphenyl)-3-(4-dimethylaminophenyl)-(4-diethylamino-2-methylphenyl)phthalide | black blue |

TABLE 1-continued

| Example | Benzophenone derivatives | Ethylene derivatives | Phthalide derivatives | Color |
|---|---|---|---|---|
| 11 | | | | black blue |
| 12 | | | | black blue |

TABLE 1-continued

| Example | Benzophenone derivatives | Ethylene derivatives | Phthalide derivatives | Color |
|---|---|---|---|---|
| 13 | (structure) | (structure) | (structure) | black blue |
| 14 | (structure) | (structure) | (structure) | black blue |

TABLE 1-continued

| Example | Benzophenone derivatives | Ethylene derivatives | Phthalide derivatives | Color |
|---|---|---|---|---|
| 15 | | | | blue |
| 16 | | | | black blue |

TABLE 1-continued

| Example | Benzophenone derivatives | Ethylene derivatives | Phthalide derivatives | Color |
|---|---|---|---|---|
| 17 | (structure) | (structure) | (structure) | black blue |
| 18 | (structure) | (structure) | (structure) | black blue |

TABLE 1-continued

| Example | Benzophenone derivatives | Ethylene derivatives | Phthalide derivatives | Color |
|---|---|---|---|---|
| 19 | | | | blue green |
| 20 | | | | blue green |

TABLE 1-continued

| Example | Benzophenone derivatives | Ethylene derivatives | Phthalide derivatives | Color |
|---|---|---|---|---|
| 21 | | | | blue green |
| 22 | | | | blue violet |

TABLE 1-continued

| Example | Benzophenone derivatives | Ethylene derivatives | Phthalide derivatives | Color |
|---|---|---|---|---|
| 23 | (structure) | (structure) | (structure) | blue violet |
| 24 | (structure) | (structure) | (structure) | blue green |

TABLE 1-continued

| Example | Benzophenone derivatives | Ethylene derivatives | Phthalide derivatives | Color |
|---------|--------------------------|----------------------|----------------------|-------|
| 25 | [structure with NO₂, COOH, C=O, phenyl with N(CH₂CH₂)₂] | [structure with two p-(dimethylamino)phenyl groups, C=CH₂] | [phthalide structure with two p-(dimethylamino)phenyl groups, pyrrolidinyl phenyl, and nitro-methylphenyl substituent] | blue green |
| 26 | [structure with Cl₄, COOH, C=O, phenyl with N(CH₂CH₂)₂] | [structure with two p-(dimethylamino)phenyl groups, C=CH₂] | [phthalide structure with two p-(dimethylamino)phenyl groups, pyrrolidinyl phenyl, and tetrachloromethylphenyl substituent] | blue green |

EXAMPLE 27

A heat-sensitive record material was prepared by the following method with the use of 3-(p-methoxyphenyl)-3-{1,1-bis(p-dimethylaminophenyl)ethylene-2-yl}-6-dimethylaminophthalide obtained in Example 1.

(1) Preparation of A liquid:
The following composition was passed through a sand mill.

| | |
|---|---|
| phthalide derivative obtained in Example 1 | 5 parts |
| stearic acid amide | 1 part |
| 2% aqueous solution of hydroxyethylcellulose | 25 parts |

Pulverization was continued until an average particle size of 2 microns.

(2) Preparation of B liquid:
The following composition was passed through a sand mill.

| | |
|---|---|
| 4,4'-isopropylidenediphenol | 50 parts |
| stearic acid amide | 10 parts |
| 2% aqueous solution of hydroxyethylcellulose | 250 parts |

Pulverization was continued until an average particle size of 2 microns.

(3) Making a heat-sensitive record material:
The following composition was mixed to prepare a coating composition.

| | |
|---|---|
| A liquid | 62 parts |
| B liquid | 31 parts |
| ultrafinely divided particles of silicic anhydride ("Syloid 244" manufactured by Fuji-Davidson Chemical) | 25 parts |
| 20% aqueous solution of a salt of styrene-maleic anhydride copolymer | 175 parts |
| zinc stearate | 5 parts |
| water | 100 parts |

The coating composition was coated on a base sheet of 50 g/m$^2$ in the weight of an amount of 6 g/m$^2$ on dry basis to obtain a heat-sensitive record material.

The heat-sensitive record material was pressed with a pressure of 4 kg/cm$^2$ for 5 seconds on a plate heated at 125° C. to develop black blue images. The colour images were superior in light resistance. The color change and discoloration when exposed to sunlight were not substantially appreciated. The light absorption spectrum of the color images had a strong maximum absorption at 510 nm and a broad strong absorption at 580–800 nm.

EXAMPLE 28

Example 27 was repeated except that 3-phenyl-3-{1,1-bis(p-dimethylaminophenyl)ethylene-2-yl}-phthalide obtained in Example 9 was used instead of 3-(p-methoxyphenyl)-3-{1,1-bis(p-dimethylaminophenyl)ethylene-2-yl}-6-dimethylaminophthalide to obtain a heat-sensitive record material and to develop color images. The color images were blue violet and superior in light resistance. The light absorption spectrum of the color images had strong maximum absorptions at 575 nm and 675 nm and a broad absorption at 700–750 nm.

EXAMPLE 29

A pressure-sensitive record material was prepared by the following method with the use of 3-p-pyrrolidinophenyl-3-{1,1-bis(p-dimethylaminophenyl)ethylene-2-yl}-6-pyrrolidinophthalide obtained in Example 23.

3 parts of the above phthalide derivative was dissolved in 100 parts of isopropylated naphthalene. The resultant solution was dispersed in 350 parts of warm water (50° C.) containing 25 parts of pigskin-gelatin having an isoelectric point of 8 and 25 parts of gum arabic dissolved in it to obtain an emulsion. 1000 parts of warm water was added to the emulsion. The mixture was adjusted to pH 4 with acetic acid and cooled at 10° C. 10 parts of 25% aqueous solution of glutaraldehyde was added to it to solidify capsules. The capsule-containing coating composition was coated on one surface of a base sheet of 45 g/m$^2$ in the weight of 5 g/m$^2$ on dry basis and an acceptor coating composition comprising 20 parts of zinc 3,5-bis(α-methylbenzyl)salicylate, 80 parts of kaolin and 30 parts of styrene-butadiene copolymer emulsion (solid content: 50%) dispersed in 200 parts of water was coated on another surface of the base sheet in the weight of 5 g/m$^2$ on dry basis to obtain a pressure-sensitive record material (middle sheet).

Several of the pressure-sensitive record material were piled in the manner as the capsule coated layer was closed to the acceptor coated layer, pressed with driving a pen to obtain blue color images on the acceptor coated surface. The color images were stable to water and alcohol and when exposed to sunlight the color change and discolouration were not appreciated. The light absorption spectrum had strong maximum absorptions at 595 nm, 670 nm and 760 nm.

EXAMPLE 30

Example 29 was repeated except that 3 parts of 3-p-pyrrolidinophenyl-3-{1,1-bis(p-dimethylaminophenyl)ethylene-2-yl}phthalide obtained in Example 19 was used instead of 3 parts of 3-p-pyrrolidinophenyl-3-{1,1-bis(p-dimethylaminophenyl)ethylene-2-yl}-6-pyrrolidinophthalide to obtain a pressure-sensitive record material and to develop color images. The color images were superior in light resistance and the light absorption spectrum of the color images had strong maximum absorptions at 650 nm and 750 nm and a week maximum absorption at 460 nm.

EXAMPLE 31

An electrothermal record material was prepared by the following method with the use of the phthalide derivative obtained in Example 2.

200 parts of cuprous iodide and 5 parts of 10% aqueous solution of sodium sulfite were added to 200 parts of 1% aqueous solution of polyvinyl alcohol. The mixture was passed through a sand mill. Pulverization was continued until an average particle size of 2 microns. To the pulverized mixture 8 parts of polyacrylate emulsion and 20 parts of titanium dioxide were added and thoroughly dispersed. The dispersion was coated on a base sheet of 50 g/m$^2$ in the weight of 7 g/m$^2$ on dry basis. Further, there was coated on the coating layer in the weight of 5 g/m$^2$ on dry basis a heat-sensitive coating composition prepared by the same manner as in Example 27 except that 3-(3,4-dimethoxyphenyl)-3-{1,1-bis(p-dimethylaminophenyl)ethylene-2-yl}-6-dimethylaminophthalide obtained in Example 2 was used instead of 3-(p- methoxyphenyl)-3-{1,1-bis(p-dimethylaminophenyl-)ethylene-2-yl}-6-dimethylaminophthalide to obtain an electrothermal record material.

Images were recorded on the record material with the use of a cylindrical scanning recording machine at a scanning speed of 630 mm/sec with a needle pressure of 10 g. The recorded images were dark blue and superior in light resistance. The light absorption spectrum of them had a strong maximum absorption at 500 nm and a strong broad absorption at 600-800 nm.

EXAMPLE 32

A photosensitive record material was prepared by the following method with the use of the phthalide derivative obtained in Example 8.

6 g of 3-(2,4-dimethoxyphenyl)-3-{1,1-bis(p-dimethylaminophenyl)ethylene-2-yl}-6-dimethylaminophthalide obtained in Example 8 was dissolved in 40 ml of chloroform. 40 ml of 10% benzene solution of polystyrene and 5 g of carbon tetrabromide were added to the solution and the mixture was thoroughly stirred to prepare a coating composition. The coating composition was coated on polyethylene laminated paper having polyethylene at the both surfaces in the weight of 5 g/m² on dry basis in a dark place. The coated paper was irradiated with a light of eight ultraviolet lamps of 20 W from a distance of 5 cm for 10 minutes to develop blue colour images. The color images were then fixed by rinsing with a solution of acetone/n-hexane (1/5). The resultant images were stable when exposed to sunlight and the light absorption spectrum had a strong maximum absorption at 530 nm and a strong broad absorption at 600-800 nm.

EXAMPLE 33

An ultrasonic vibrator of needle type having a radius of 0.2 nm was slightly contacted on a surface of the heat-sensitive record material obtained in Example 27 and the record material was moved at a speed of 20 cm/sec under an ultrasonic vibration of 19 KHz 20 W to obtain blue recorded images superior in light resistance.

EXAMPLE 34

3.3 g of phthalic anhydride and 12.8 g of 1,1-bis(4-pyrrolidinophenyl)ethylene were added to 25 g of acetic anhydride and the mixture was reacted at 80° C. for one hour. After the termination of reaction, the product was poured into water and then neutralized with an aqueous solution of ammonium to decompose acetic anhydride. The resultant precipitate was separated by filtration, dried and recrystallized from ethanol to obtain 6.7 g of 3,3-bis{1,1-bis(4-pyrrolidinophenyl)ethylene-2-yl}phthalide in the form of light green crystals having a melting point of 198°-201° C. The phthalide derivative became blue green upon contact with silica gel.

EXAMPLE 35

Example 34 was repeated except that 6.3 g of 3,4,5,6-tetrachlorophthalic anhydride was used instead of 3,3 g of phthalic anhydride to obtain 14.2 g of 3,3-bis{1,1-bis(4-pyrrolidinophenyl)ethylene-2-yl}-4,5,6,7-tetrachlorophthalide in the form of light green crystals having a melting point of 222°-227° C. The phthalide derivative became green upon contact with silica gel.

EXAMPLE 36

Example 34 was repeated except that 6.3 g of 3,4,5,6-tetrachlorophthalic anhydride was used instead of 3.3 g of phthalic anhydride and 13.8 g of 1,1-bis(4-piperidinophenyl)ethylene was used instead of 12.8 g of 1,1-bis(4-pyrrolidinophenyl)ethylene to obtain 11.7 g of 3,3-bis{1,1-bis(4-piperidinophenyl)ethylene-2-yl}-4,5,6,7-tetrachlorophthalide in the form of light green crystals having a melting point of 213°-217° C. The phthalide derivative became green upon contact with silica gel.

EXAMPLES 37-52

Example 34 was repeated except that phthalic anhydride derivatives shown in Table 2 were used instead of phthalic anhydride and ethylene derivatives shown in Table 2 were used instead of 1,1-bis(4-pyrrolidinophenyl)ethylene to obtain phthalide derivatives shown in Table 2. The colors formed upon contact with silica gel are shown in Table 2.

TABLE 2

| Example | phthalic anhydride derivatives | ethylene derivatives | phthalide derivatives | color |
|---|---|---|---|---|
| 37 | 4-nitrophthalic anhydride | 1,1-bis(4-pyrrolidinophenyl)ethylene | 3,3-bis{1,1-bis(4-pyrrolidinophenyl)ethylene-2-yl}-5-nitrophthalide<br>3,3-bis{1,1-bis(4-pyrrolidinophenyl)ethylene-2-yl}-6-nitrophthalide | green |
| 38 | 4-ethoxyphthalic anhydride | 1,-bis(4-pyrrolidinophenyl)ethylene | 3,3-bis{1,1-bis(4-pyrrolidinophenyl)ethylene-2-yl}-5-ethoxyphthalide<br>3,3-bis{1,1-bis(4-pyrrolidinophenyl)ethylene-2-yl}-6-ethoxyphthalide | blue green |
| 39 | 4-methylphthalic anhydride | 1,1-bis(4-pyrrolidinophenyl)ethylene | 3,3-bis{1,1-bis(4-pyrrolidinophenyl)ethylene-2-yl}-5-methylphthalide<br>3,3-bis{1,1-bis(4-pyrrolidinophenyl)ethylene-2-yl}-6-methylphthalide | blue green |
| 40 | 4-pyrrolidinophthalic anhydride | 1,1-bis(4-pyrrolidinophenyl)ethylene | 3,3-bis{1,1-bis(4-pyrrolidinophenyl ethylene-2-yl}-5-pyrrolidinophthalide<br>3,3-bis{1,1-bis(4-pyrrolidinophenyl)ethylene-2-yl}-6-pyrrolidinophthalide | green blue |
| 41 | 4,5-dichlorophthalic | 1,1-bis(4-pyrrolidino- | 3,3-bis{1,1-bis(4-pyrrolidino- | green |

TABLE 2-continued

| Example | phthalic anhydride derivatives | ethylene derivatives | phthalide derivatives | color |
|---|---|---|---|---|
| | anhydride | phenyl)ethylene | phenyl)ethylene-2-yl}-5,6-dichlorophthalide | |
| 42 | phthalic anhydride | 1,1-bis(4-piperidino-phenyl)ethylene | 3,3-bis{1,1-bis(4-piperidino-phenyl)ethylene-2-yl}phthalide | blue green |
| 43 | 4-dimethylamino-phthalic anhydride | 1,1-bis(4-piperidino-phenyl)ethylene | 3,3-bis{1,1-bis(4-piperidino-phenyl)ethylene-2-yl}-5-dimethyl-aminophthalide  3,3-bis{1,1-bis(4-piperidino-phenyl)ethylene-2-yl}-6-dimethyl-aminophthalide | green blue |
| 44 | 3,4,5,6-tetra-chlorophthalic anhydride | 1,1-bis(4-piperidino-phenyl)ethylene | 3,3-bis{1,1-bis(4-piperidino-phenyl)ethylene-2-yl}-4,5,6,7-tetrachlorophthalide | green |
| 45 | 3,4,5,6-tetrachloro-phthalic anhydride | 1,1-bis(4-morpholino-phenyl)ethylene | 3,3-bis{1,1-bis(4-morpholino-phenyl)ethylene-2-yl}-4,5,6,7-tetrachlorophthalide | green |
| 46 | 3,4,5,6-tetrachloro-phthalic anhydride | 1,1-bis(4-hexa-methyleneiminophenyl)-ethylene | 3,3-bis{1,1-bis(4-hexamethylene-iminophenyl)ethylene-2-yl}-4,5,6,7-tetrachlorophthalide | green |
| 47 | 3,4,5,6-tetrachloro-phthalic anhydride | 1,1-bis(2-methyl-4-pyrrolidinophenyl)-ethylene | 3,3-bis{1,1-bis(2-methyl-4-pyrrolidinophenyl)ethylene-2-yl}-4,5,6,7-tetrachloro-phthalide | green |
| 48 | 3,4,5,6-tetrachloro-phthalic anhydride | 1,1-bis(2-methoxy-4-pyrrolidinophenyl)-ethylene | 3,3-bis{1,1-bis(2-methoxy-4-pyrrolidinophenyl)ethylene-2-yl}-4,5,6,7-tetrachloro-phthalide | green |
| 49 | 3,4,5,6-tetrachloro-phthalic anhydride | 1,1-bis(4-pyrrolidino-phenyl)-1-propene | 3,3-bis{1,1-bis(4-pyrrolidino-phenyl)-1-propene-2-yl}-4,5,6,7-tetrachlorophthalide | green |
| 50 | 3,4,5,6-tetrachloro-phthalic anhydride | 1-(4-pyrrolidino-phenyl)-1-(4-dimethyl-aminophenyl)ethylene | 3,3-bis{1-(4-pyrrolidinophenyl)-1-(4-dimethylaminophenyl)-ethylene-2-yl}-4,5,6,7-tetra-chlorophthalide | green |
| 51 | 3,4,5,6-tetrachloro-phthalic anhydride | 1-(4-pyrrolidino-phenyl)-1-(4-N—ethyl-N—benzylaminophenyl)-ethylene | 3,3-bis{1-(4-pyrrolidinophenyl)-1-(4-N—ethyl-N—benzylaminophenyl)-ethylene-2-yl}-4,5,6,7- tetra-chlorophthalide | green |
| 52 | 3,4,5,6-tetrachloro-phthalic anhydride | 1-(4-pyrrolidino-phenyl)-1-(4-N—methyl-N—p-tolylaminophenyl)-ethylene | 3,3-bis{1-(4-pyrrolidinophenyl)-1-(4-N—methyl-N—p-tolylamino-phenyl)ethylene-2-yl}-4,5,6,7-tetrachlorophthalide | green |

EXAMPLE 53

A heat-sensitive record material was prepared by the following method with the use of 3,3-bis[1,1-bis(4-pyrrolydinophenyl)ethylene-2-yl]phthalide obtained in Example 34.

(1) Preparation of A liquid:
The following composition was passed through a sand mill.

| | |
|---|---|
| phthalide derivative obtained in Example 34 | 5 parts |
| stearic acid amide | 1 part |
| 2% aqueous solution of hydroxyethyl-cellulose | 25 parts |

Pulverization was continued until an average particle size of 2 microns.

(2) Preparation of B liquid:
The following composition was passed through a sand mill.

| | |
|---|---|
| 4,4'-isopropylidenediphenol | 50 parts |
| stearic acid amide | 10 parts |
| 2% aqueous solution of hydroxyethyl-cellulose | 250 parts |

Pulverization was continued until an average particle size of 2 microns.

(3) Making a heat-sensitive record material:
The following composition was mixed to prepare a coating composition.

| | |
|---|---|
| A liquid | 62 parts |
| B liquid | 31 parts |
| ultrafinely divided particles of silicic anhydride ("Syloid 244" manufactured by Fuji-Davidson Chemical) | 25 parts |
| 20% aqueous solution of a salt of styrene-maleic anhydride copolymer | 175 parts |
| zinc stearate | 5 parts |
| water | 100 parts |

The coating composition was coated on a base sheet of 50 g/m$^2$ in the weight of an amount of 6 g/m$^2$ on dry basis to obtain a heat-sensitive record material.

The heat-sensitive record material was pressed with a pressure of 4 kg/cm$^2$ for 5 seconds on a plate heated at 125° C. to develop blue green images. The colour images were superior in light resistance. The colour change and discoloration when exposed to sunlight were not substantially appreciated. The light absorption spectrum of the colour images had a broad strong absorption at 600–900 nm.

EXAMPLE 54

Example 53 was repeated except that 3,3-bis[1,1-bis(4-pyrrolidinophenyl)ethylene-2-yl]-4,5,6,7-tetrachlorophthalide obtained in Example 35 was used instead of 3,3-bis[1,1-bis(4-pyrrolidinophenyl)ethylene-2-yl]phthalide to obtain a heat-sensitive record material and to develop colour images. The colour images were green and superior in light resistance. The light absorption spectrum of the colour images had a strong absorption at 475 nm and a broad absorption at 620–900 nm.

EXAMPLE 55

A pressure-sensitive record material was prepared by the following method with the use of the mixture of 3,3-bis[1,1-bis(4-pyrrolidinophenyl)ethylene-2-yl]-5-pyrrolidinophthalide and 3,3-bis[1,1-bis(4-pyrrolidinophenyl)ethylene-2-yl]-6-pyrrolidinophthalide obtained in Example 40.

3 parts of the above phthalide derivative was dissolved in 100 parts of isopropylated naphthalene. The resultant solution was dispersed in 350 parts of warm water (50° C.) containing 25 parts of pigskin-gelatin having an isoelectric point of 8 and 25 parts of gum arabic dissolved in it to obtain an emulsion. 1000 parts of warm water was added to the emulsion. The mixture was adjusted to pH 4 with acetic acid and cooled at 10° C. 10 parts of 25% aqueous solution of glutaraldehyde was added to it to solidify capsules. The capsule-containing coating composition was coated on one surface of a base sheet of 45 g/m$^2$ in the weight of 5 g/m$^2$ on dry basis and an acceptor coating composition comprising 20 parts of zinc 3,5-bis($\alpha$-methylbenzyl)salicylate, 80 parts of kaolin and 30 parts of styrene-butadiene copolymer emulsion (solid content: 50%) dispersed in 200 parts of water was coated on another surface of the base sheeet in the weight of 5 g/m$^2$ on dry basis to obtain a pressure-sensitive record material (middle sheet).

Several of the pressure-sensitive record material were piled in the manner as the capsule coated layer was closed to the acceptor coated layer, pressed with driving a pen to develop blue green color images on the acceptor coated surface. The color images were stable to water and alcohol and when exposed to sunlight the color change and discolouration were not appreciated. The light absorption spectrum had a broad strong absorption at 590–900 nm.

EXAMPLE 56

Example 55 was repeated except that 3 parts of the mixture of 3,3-bis[1,1-bis(piperidinophenyl)ethylene-2-yl]-5-dimethylaminophthalide and 3,3-bis[1,1-bis(4-piperidinophenyl)ethylene-2-yl]-6-dimethylaminophthalide obtained in Example 43 to obtain a pressure-sensitive record material and to develop color images. The color images were superior in light resistance and the light absorption spectrum of them had a broad strong absorption at 595–900 nm.

EXAMPLE 57

An electrothermal record material was prepared by the following method with the use of the phthalide derivative obtained in Example 36.

200 parts of cuprous iodide and 5 parts of 10% aqueous solution of sodium sulfite were added to 200 parts of 1% of aqueous solution of polyvinylalcohol. The mixture was passed through a sand mill. Pulverization was continued until an average particle size of 2 microns. To the pulverized mixture 8 parts of polyacrylate emulsion and 20 parts of titanium dioxide were added and thoroughly dispersed. The dispersion was coated on a base sheet of 50 g/m$^2$ in the weight of 7 g/m$^2$ on dry basis. Furrther, there was coated on the coating layer in the weight of 5 g/m$^2$ on dry basis a heat-sensitive coating composition prepared by the same manner as in Example 53 except that 3,3-bis[1,1-bis(4-piperidinophenyl)ethylene-2-yl]-4,5,6,7-tetrachlorophthalide obtained in Example 36 was used instead of 3,3-bis[1,1-bis(4-pyrrolidinophenyl)ethylene-2-yl]phthalide to obtain an electrothermal record material.

Images were recorded on the record material with the use of a cylindrical scanning recording machine at a scanning speed of 630 mm/sec with a needle pressure of 10 g. The recorded images were dark blue and superior in light resistance. The light absorption spectrum of them had a strong absorption at 470 nm and a broad strong absorption at 620–900 nm.

EXAMPLE 58

A phothosensitive record material was prepared by the following method with the use of phthalide derivative obtained in Example 50.

6 g of 3,3-bis[1-(4-pyrrolidinophenyl)-1-(4-dimethylaminophenyl)ethylene-2-yl]-4,5,6,7-tetrachlorophthalide obtained in Example 50 was dissolved in 40 ml of chloroform. 40 ml of 10% benzene solution of polystyrene and 5 g of carbon tetrabromide were added to the solution and the mixture was thoroughly stirred to prepare a coating composition. The coating composition was coated on polyethylene laminated paper having polyethylene at the both surfaces in the weight of 5 g/m$^2$ on dry basis in a dark place. The coated paper was irradiated with a light of eight ultraviolet lamps of 20 W from a distance of 5 cm for 10 minutes to develop green colour images. The color images were then fixed by rinsing with a solution of acetone/n-hexane(1/5). The resultant images were stable when exposed to sunlight and the light absorption spectrum had a strong absorption at 475 nm and a broad strong absorption at 625–900 nm.

EXAMPLE 59

An ultrasonic vibrator of needle type having a radius of 0.2 mm was slightly contacted on a surface of the heat-sensitive record material obtained in Example 54 and the record material was moved at a speed of 20 cm/sec under an ultrasonic vibration of 19 KHz 20 W to obtain green recorded images superior in light resistance.

What we claim is:

1. A recording system which utilizes the color forming reaction between a colorless chromogenic material and an electron accepting acidic reactant material, characterized in that said colorless chromogenic material comprises at least one phthalide derivative having the formula:

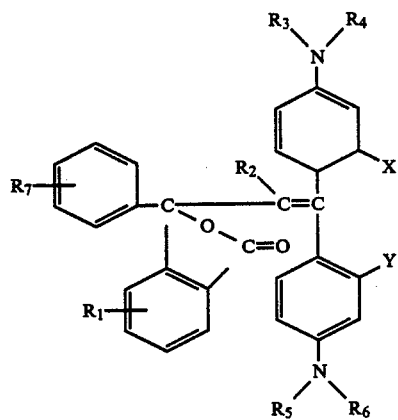

wherein $R_1$ is hydrogen or at least one substituent selected from the group consisting of halogen, $C_1 \sim C_4$ alkyl, $C_1 \sim C_4$ alkoxyl, nitro, and amino having the formula

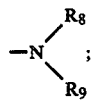

$R_2$ is hydrogen or $C_1 \sim C_4$ alkyl; each $R_3$, $R_4$, $R_5$, $R_6$, $R_8$, and $R_9$ is hydrogen, $C_1 \sim C_4$ alkyl, benzyl, halogen substituted benzyl, phenyl, or $C_1 \sim C_4$ alkyl or $C_1 \sim C_2$ alkoxyl subtituted phenyl, or both of $R_3$ and $R_4$, $R_5$ and $R_6$ or $R_8$ and $R_9$ together with the adjacent nitrogen form an alicyclic amino having the formula

c is an integer of 4 to 6; $R_7$ is hydrogen or one to two substituents selected from the group consisting of halogen, $C_1 \sim C_4$ alkyl, $C_1 \sim C_4$ alkoxyl, nitro and alicyclic amino having the formula

c is an integer of 4 to 6; and each X and Y is hydrogen, $C_1 \sim C_4$ alkyl or $C_1 \sim C_4$ alkoxyl.

2. A recording system as defined in claim 1, wherein X, $R_3$ and $R_4$ are the same as Y, $R_5$ and $R_6$, respectively.

3. A recording system as defined in claim 1, wherein said phthalide derivative has the formula:

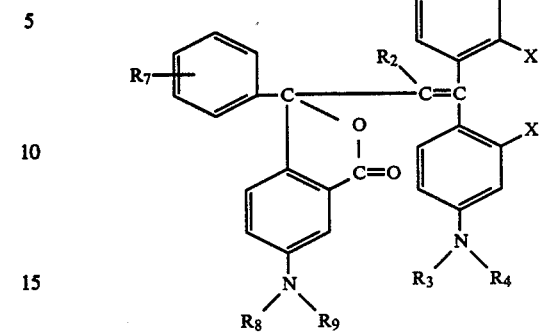

wherein $R_2$, $R_3$, $R_4$, $R_7$, $R_8$, $R_9$, and X are the same as hereinabove defined.

4. A recording system as defined in claim 1, wherein said phthalide derivative has the formula:

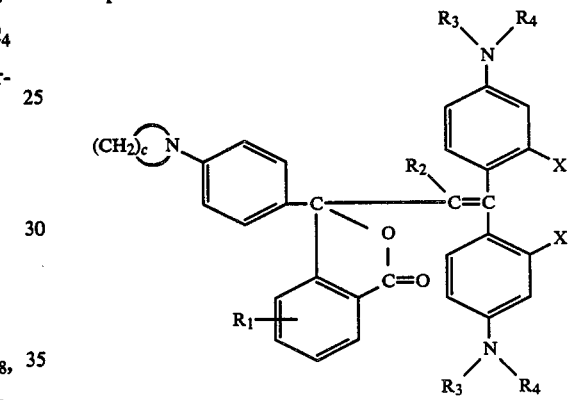

wherein $R_1$, $R_2$, $R_3$, $R_4$, and c are the same as hereinabove defined.

5. A recording system as defined in claim 1, wherein said recording system is a pressure-sensitive recording system.

6. A recording system as defined in claim 1, wherein said recording system is a heat-sensitive recording system.

7. A recording system as defined in claim 1, wherein said phthalide derivative has the formula:

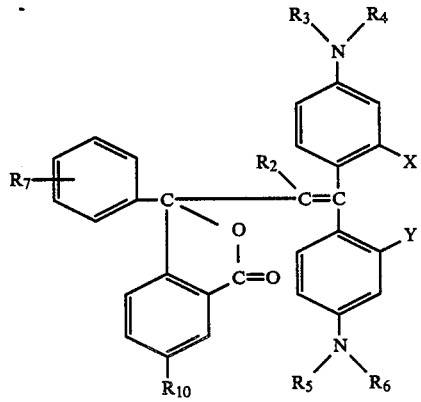

wherein $R_{10}$ is hydrogen or amino having the formula

and $R_2$, $R_3$, $R_4$, $R_5$, $R_6$, $R_7$, $R_8$, $R_9$, X and Y are the same as hereinabove defined.

* * * * *

UNITED STATES PATENT AND TRADEMARK OFFICE
CERTIFICATE OF CORRECTION

PATENT NO. : 4,748,148

DATED : May 31, 1988

INVENTOR(S) : Mitsuru Kondo, Tomoyuki Okimoto and Nobuo Kanda

It is certified that error appears in the above-identified patent and that said Letters Patent is hereby corrected as shown below:

On the title page, insert the assignee as follows:

[73] Assignee: Kanzaki Paper Manufacturing Co., Ltd., Tokyo, Japan

Signed and Sealed this

Twenty-ninth Day of November, 1988

Attest:

DONALD J. QUIGG

*Attesting Officer*   *Commissioner of Patents and Trademarks*